(12) United States Patent
Wang et al.

(10) Patent No.: US 7,723,043 B2
(45) Date of Patent: May 25, 2010

(54) METHODS FOR SCREENING FOR PROSTATE CANCER

(75) Inventors: Bruce Wang, Mountain View, CA (US); Matthias Wabl, San Francisco, CA (US)

(73) Assignee: Picobella, LP, Burlingame, CA (US)

( * ) Notice: Subject to any disclaimer, the term of this patent is extended or adjusted under 35 U.S.C. 154(b) by 0 days.

(21) Appl. No.: 11/325,847

(22) Filed: Jan. 4, 2006

(65) Prior Publication Data

US 2007/0154964 A1  Jul. 5, 2007

(51) Int. Cl.
  G01N 33/53 (2006.01)
  G01N 33/567 (2006.01)
  G01N 33/574 (2006.01)
  C07K 16/00 (2006.01)

(52) U.S. Cl. ............... 435/7.1; 435/7.21; 435/7.23; 530/387.1; 530/387.7

(58) Field of Classification Search ............... None
See application file for complete search history.

(56) References Cited

U.S. PATENT DOCUMENTS

2004/0236080 A1  11/2004  Aburatani et al.

FOREIGN PATENT DOCUMENTS

| EP | 1 541 680 A1 | 6/2005 |
| EP | 1 548 442 A1 | 6/2005 |
| WO | WO2004038420 | * 9/2003 |

OTHER PUBLICATIONS

Stites et al (Basic and Clinical Immunology, 9th Ed, Appleton and Lange, Norwalk, 1991, p. 250-251).*
Yoshitaka et al. (2004, Cancer Research 64:2418-2423).*
Heller, M.J., "DNA Microarray Technology: Devices, Systems, and Applications", *Annual Review Biomedical Engineering*, 4:129-153 (2002).
Capurro et al., "Glypican-3 promotes the growth of hepatocellular carcinoma by stimulating canonical Wnt signaling", *Cancer Res.*, 65:6245-54 (2005).
Collier et al., "Cancer gene discovery in solid tumours using transposon-based somatic mutagenesis in the mouse", *Nature*, 436:272-276 (2005).
Dupuy et al., "Mammalian mutagenesis using a highly mobile somatic Sleeping Beauty transposon system", *Nature*, 436:221-226 (2005).
Filmus, J., and S. B. Selleck, "Glypicans: proteoglycans with a surprise", *J Clin Invest*, 108:497-501 (2001).
Grisaru et al., "Glypican-3 modulates BMP- and FGF-mediated effects during renal branching morphogenesis", *Dev. Biol.*, 231:31-46 (2001).
Hsu et al., "Cloning and expression of a developmentally regulated transcript MXR7 in hepatocellular carcinoma: biological significance and temporospatial distribution", *Cancer Res*, 57:5179-5184 (1997).
Kim et al., "The heparan sulfate proteoglycan GPC3 is a potential lung tumor suppressor",. *Am J Respir Cell Mol Biol*, 29:694-701(2003).
Lin et al.,"Frequent silencing of the GPC3 gene in ovarian cancer cell lines", *Cancer Res*, 59:807-810 (1999).
Lund et al., "Genome-wide retroviral insertional tagging of genes involved in cancer in Cdkn2a-deficient mice", *Nat Genet*, 32:160-165 (2002).
Midorikawa et al., "Glypican-3, overexpressed in hepatocellular carcinoma, modulates FGF2 and BMP-7 signaling", *Int J Cancer*, 103:455-465 (2003).
Mikkers et al. "High-throughput retroviral tagging to identify components of specific signaling pathways in cancer",. *Nat Genet*, 32:153-159 (2002).
Murthy et al. "Expression of GPC3, an X-linked recessive overgrowth gene, is silenced in malignant mesothelioma", *Oncogene*, 19:410-416 (2000).
Nakatsura et al., *Biochemical and Biophysical Research Communications*, 306(1):16-25 (2004).
Nakatsura et al., "Identification of glypican-3 as a novel tumor marker for melanoma", *Clin Cancer Res*, 10:6612-6621 (2004).
Nusse et al., "Mode of proviral activation of a putative mammary oncogene (int-1) on mouse chromosome 15",. *Nature*, 307:131-136 (1984).
Nusse, R., and H. E. Varmus, "Many tumors induced by the mouse mammary tumor virus contain a provirus integrated in the same region of the host genome",. *Cell* 31:99-109 (1982).
Paine-Saunders et al., "Glypican-3 controls cellular responses to Bmp4 in limb patterning and skeletal development", *Dev Biol.*, 225:179-187 (2000).
Powell, et al., "Oligonucleotide microarray analysis of lung adenocarcinoma in smokers and nonsmokers identifies GPC3 as a potential lung tumor suppressor", *Chest* 121:6S-7S (2002).
Saikali, Z., and D. Sinnett, "Expression of glypican 3 (GPC3) in embryonal tumors", *Int J Cancer*, 89:418-422 (2000).
Sorensen et al., "Sequence tags of provirus integration sites in DNAs of tumors induced by the murine retrovirus SL3-3" *J Virol*, 70:4063-4070 (1996).
Sung et al., "Glypican-3 is overexpressed in human hepatocellular carcinoma",. *Cancer Sci*, 94:259-262 (2003).
Veugelers et al., *Human Molecular Genetics*, 9(9):1321-1328 (2000).
Xiang et al., "Glypican-3 expression is silenced in human breast cancer",. *Oncogene*, 20:7408-7412 (2000).

(Continued)

*Primary Examiner*—Peter J Reddig
(74) *Attorney, Agent, or Firm*—King & Spalding LLP; Susan J. Myers Fitch; Peter J. Dehlinger

(57) ABSTRACT

Methods for diagnosing and treating prostate cancer are disclosed. In practicing the method, a subject's body-fluid sample is assayed for GPC3 protein, and the GPC3 level observed is used in determining whether the subject has an elevated GPC3 level associated with prostate cancer. Patients with such elevated levels may be treated, in accordance with the invention, with a variety of GPC3-related immunotherapy agents.

4 Claims, 3 Drawing Sheets

OTHER PUBLICATIONS

Yamauchi et al., "The glypican 3 oncofetal protein is a promising diagnostic marker for hepatocellular carcinoma", *Mod Pathol.*, 18:1591-1598 (2005).

Zhang et al., "Membrane heparan sulfate proteoglycan-supported FGF2-FGFR1 signaling: evidence in support of the "cooperative end structures" model", *J Biol Chem.*, 276(45):41921-41929 (2001).

Zhu et al., "Enhanced glypican-3 expression differentiates the majority of hepatocellular carcinomas from benign hepatic disorders",. *Gut*, 48:558-564 (2001).

Zhu et al., "Glypican-3 expression is markedly decreased in human gastric cancer but not in esophageal cancer", *Am J Surg*, 184:78-83 (2002).

\* cited by examiner prostate tumor matched normal prostate

```
SEQUENCE LISTING

<160> NUMBER OF SEQ ID NOS: 2

<210> SEQ ID NO 1
<211> LENGTH: 19
<212> TYPE: PRT
<213> ORGANISM: Homo sapiens

<400> SEQUENCE: 1

Asp Leu Phe Ile Asp Lys Lys Val Leu Lys Val Ala His Val Glu His
1               5                   10                  15

Glu Glu Thr

<210> SEQ ID NO 2
<211> LENGTH: 16
<212> TYPE: PRT
<213> ORGANISM: Homo sapiens

<400> SEQUENCE: 2

Leu Ala Tyr Asp Leu Asp Val Asp Asp Ala Pro Gly Asn Ser Gln Gln
1               5                   10                  15
```

METHODS FOR SCREENING FOR PROSTATE CANCER

FIELD OF THE INVENTION

This invention relates generally to methods for diagnosing and treating prostate cancer.

REFERENCES

The following references are cited below in support of the background of the invention or methods employed in practicing the invention.
1. Filmus, J., and S. B. Selleck. 2001. Glypicans: proteoglycans with a surprise. *J Clin Invest* 108:497.
2. Zhang, Z., C. Coomans, and G. David. 2001. Membrane heparan sulfate proteoglycan-supported FGF2-FGFR1 signaling: evidence in support of the "cooperative end structures" model. *J Biol Chem* 276:41921.
3. Capurro, M. I., Y. Y. Xiang, C. Lobe, and J. Filmus. 2005. Glypican-3 promotes the growth of hepatocellular carcinoma by stimulating canonical Wnt signaling. *Cancer Res* 65:6245.
4. Grisaru, S., D. Cano-Gauci, J. Tee, J. Filmus, and N. D. Rosenblum. 2001. Glypican-3 modulates BMP- and FGF-mediated effects during renal branching morphogenesis. *Dev Biol* 231:31.
5. Paine-Saunders, S., B. L. Viviano, J. Zupicich, W. C. Skarnes, and S. Saunders. 2000. glypican-3 controls cellular responses to Bmp4 in limb patterning and skeletal development. *Dev Biol* 225:179.
6. Yamauchi, N., A. Watanabe, M. Hishinuma, K. I. Ohashi, Y. Midorikawa, Y. Morishita, T. Niki, J. Shibahara, M. Mori, M. Makuuchi, Y. Hippo, T. Kodama, H. Iwanari, H. Aburatani, and M. Fukayama. 2005. The glypican 3 oncofetal protein is a promising diagnostic marker for hepatocellular carcinoma. *Mod Pathol*.
7. Powell, C. A., G. Xu, J. Filmus, S. Busch, J. S. Brody, and P. B. Rothman. 2002. Oligonucleotide microarray analysis of lung adenocarcinoma in smokers and nonsmokers identifies GPC3 as a potential lung tumor suppressor. *Chest* 121:6S.
8. Kim, H., G. L. Xu, A. C. Borczuk, S. Busch, J. Filmus, M. Capurro, J. S. Brody, J. Lange, J. M. D'Armiento, P. B. Rothman, and C. A. Powell. 2003. The heparan sulfate proteoglycan GPC3 is a potential lung tumor suppressor. *Am J Respir Cell Mol Biol* 29:694.
9. Zhu, Z., H. Friess, J. Kleeff, L. Wang, M. Wirtz, A. Zimmermann, M. Korc, and M. W. Buchler. 2002. Glypican-3 expression is markedly decreased in human gastric cancer but not in esophageal cancer. *Am J Surg* 184:78.
10. Lin, H., R. Huber, D. Schlessinger, and P. J. Morin. 1999. Frequent silencing of the GPC3 gene in ovarian cancer cell lines. *Cancer Res* 59:807.
11. Murthy, S. S., T. Shen, A. De Rienzo, W. C. Lee, P. C. Ferriola, S. C. Jhanwar, B. T. Mossman, J. Filmus, and J. R. Testa. 2000. Expression of GPC3, an X-linked recessive overgrowth gene, is silenced in malignant mesothelioma. *Oncogene* 19:410.
12. Xiang, Y. Y., V. Ladeda, and J. Filmus. 2001. Glypican-3 expression is silenced in human breast cancer. *Oncogene* 20:7408.
13. Sung, Y. K., S. Y. Hwang, M. K. Park, M. Farooq, I. S. Han, H. I. Bae, J. C. Kim, and M. Kim. 2003. Glypican-3 is overexpressed in human hepatocellular carcinoma. *Cancer Sci* 94:259.
14. Hsu, H. C., W. Cheng, and P. L. Lai. 1997. Cloning and expression of a developmentally regulated transcript MXR7 in hepatocellular carcinoma: biological significance and temporospatial distribution. *Cancer Res* 57:5179.
15. Zhu, Z. W., H. Friess, L. Wang, M. Abou-Shady, A. Zimmermann, A. D. Lander, M. Korc, J. Kleeff, and M. W. Buchler. 2001. Enhanced glypican-3 expression differentiates the majority of hepatocellular carcinomas from benign hepatic disorders. *Gut* 48:558.
16. Lage, H., M. Dietel, G. Froschle, and A. Reymann. 1998. Expression of the novel mitoxantrone resistance associated gene MXR7 in colorectal malignancies. *Int J Clin Pharmacol Ther* 36:58.
17. Saikali, Z., and D. Sinnett. 2000. Expression of glypican 3 (GPC3) in embryonal tumors. *Int J Cancer* 89:418.
18. Midorikawa, Y., S. Ishikawa, H. Iwanari, T. Imamura, H. Sakamoto, K. Miyazono, T. Kodama, M. Makuuchi, and H. Aburatani. 2003. Glypican-3, overexpressed in hepatocellular carcinoma, modulates FGF2 and BMP-7 signaling. *Int J Cancer* 103:455.
19. Nakatsura, T., T. Kageshita, S. Ito, K. Wakamatsu, M. Monji, Y. Ikuta, S. Senju, T. Ono, and Y. Nishimura. 2004. Identification of glypican-3 as a novel tumor marker for melanoma. *Clin Cancer Res* 10:6612.
20. Nusse, R., A. van Ooyen, D. Cox, Y. K. Fung, and H. Varmus. 1984. Mode of proviral activation of a putative mammary oncogene (int-1) on mouse chromosome 15. *Nature* 307:131.
21. Nusse, R., and H. E. Varmus. 1982. Many tumors induced by the mouse mammary tumor virus contain a provirus integrated in the same region of the host genome. *Cell* 31:99.
22. Sorensen, A. B., M. Duch, H. W. Amtoft, P. Jorgensen, and F. S. Pedersen. 1996. Sequence tags of provirus integration sites in DNAs of tumors induced by the murine retrovirus SL3-3. *J Virol* 70:4063.
23. Lund, A. H., G. Turner, A. Trubetskoy, E. Verhoeven, E. Wientjens, D. Hulsman, R. Russell, R. A. DePinho, J. Lenz, and M. van Lohuizen. 2002. Genome-wide retroviral insertional tagging of genes involved in cancer in Cdkn2a-deficient mice. *Nat Genet* 32:160.
24. Mikkers, H., J. Allen, P. Knipscheer, L. Romeijn, A. Hart, E. Vink, A. Berns, and L. Romeyn. 2002. High-throughput retroviral tagging to identify components of specific signaling pathways in cancer. *Nat Genet* 32:153.
25. Collier, L. S., C. M. Carlson, S. Ravimohan, A. J. Dupuy, and D. A. Largaespada. 2005. Cancer gene discovery in solid tumours using transposon-based somatic mutagenesis in the mouse. *Nature* 436:272.
26. Dupuy, A. J., K. Akagi, D. A. Largaespada, N. G. Copeland, and N. A. Jenkins. 2005. Mammalian mutagenesis using a highly mobile somatic Sleeping Beauty transposon system. *Nature* 436:221.

BACKGROUND OF THE INVENTION

Prostate cancer is the most common malignant cancer in North American men. It is estimated that approximately 200,000 new cases and 31,500 prostate cancer-related deaths will occur in the United States annually. Prostate cancer is now the second leading cause of cancer death in men, exceeded only by lung cancer. It accounts for 29% of all male cancers and 11% of male cancer-related deaths.

Currently, the FDA has approved serum PSA (prostate-specific antigen) for use as a prostate cancer screening laboratory test. Like many serum tumor markers, PSA is produced by both normal and cancerous glands. In men with prostate cancer, the serum levels can be elevated with both localized and advanced or disseminated disease. PSA levels are generally proportional to the volume of the cancer. Because there is a significant overlap between PSA levels found in cancer and benign prostatic hyperplasia, it is important to obtain sequential levels in low or borderline elevated values.

The introduction of free PSA (fPSA) testing has introduced a greater level of specificity in identifying early prostate cancer. In 1998, the FDA approved fPSA testing as a diagnostic aid for men with total PSA values between 4.0-10.0 ng/mL. This has often been the diagnostic gray zone for total PSA testing and fPSA may aid in the stratification. In general, at any free PSA level, the more enlarged the prostate, the more likely the prostate may be cancerous. However, these tests remain qualitative at best, and more reliable types of detection, and means for staging the cancer treatment, are needed.

Prostate cancer, like other forms of cancer, is caused by genetic aberrations, i.e., mutations. In the mutant cells the normal balance between the factors that promote and restrain growth is disrupted, and as a result, these mutant cells proliferate continuously—the hallmark of tumor cells. Mutations can arise spontaneously or by external factors such as chemical mutagens, radiation, or viral integration, which inserts extra-genomic DNA that may or may not contain an oncogene. A cellular gene can be modified by point mutation, insertion and frame shift (including truncation), (functional) deletion (including silencing), or translocation, which sometimes can result in gene fusion. In this way protooncogenes can become oncogenes, which promote proliferation, and tumor suppressor genes can become inactivated, also inducing tumor growth. Any combination of the above-mentioned changes in DNA can contribute to tumor formation. The consequences of these changes may or may not be held in check by the immune system (immune surveillance).

One protein whose expression has been implicated in certain cancers is the Glypican 3 protein, or GPC3, a heparin sulfate proteoglycan anchored to the cell membrane via glycosylphosphatidylinositol (1). The protein has a molecular weight of 65.6 kDa and the polypeptide chain has 580 amino acid residues. The heparin sulfate chain of the proteoglycans interacts with heparin-binding growth factors and thus serves as a co-receptor in cell signaling (2), although GPC3 might bind also in a different way (3). In embryonic development, GPC3 modulates BMP and EGF-mediated effects during renal branching morphogenesis (4). It also controls cellular responses to BMP4 in limb patterning and skeletal development (5). Except for weak expression in bronchiolar epithelial cells, GPC3 is not expressed in systemic organs (6). Because its expression is decreased in lung adenocarcinoma (7, 8), human gastric cancer (9), ovarian cancer cell lines (10, 11), mesotheliomas (10, 11), and breast tumors (12), GPC3 may function as a tumor suppressor. But because its mRNA and protein expression is increased in hepatocellular carcinomas (13-15), colorectal malignancies (16), and embryonal tumors (17) as compared to normal tissue, GPC3 is also considered an onco(fetal) protein. For hepatocarcinoma, GPC3 is a promising diagnostic marker (6). It is also known that in these cancers, GPC3 modulates FGF2 and BMP-7 signaling (18), and promotes growth by stimulating canonical Wnt signaling (3).

In more than 80% of melanoma and melanocytic nevus, both GPC3 mRNA and protein are expressed (19). Interestingly, GPC3 protein is found in sera from 40% of melanoma patients but not in sera from subjects with large congenital melanocytic nevus and from healthy donors. GPC3 expression disappeared in sera from one third of the patients after surgical removal of the melanoma (19).

Heretofore, there has been no demonstrated link between changes in GPC3 levels and prostate cancer. Such a link could have a number of important diagnostic and therapeutic applications. In accordance with the present invention, it has now been discovered that (i) GPC3 levels increase significantly in prostate cancer cells, and (ii) this increase can be measured the ductile fluid and blood-fluid sample of patients.

SUMMARY OF THE INVENTION

The invention includes, in one aspect, a method of screening for prostate cancer in a human subject, or staging treatment of prostate cancer in a subject. The method includes assaying a body-fluid sample from the subject for the level of GPC3 protein in the sample, and determining from the assayed level, whether the subject has an elevated GPC3 level associated with prostate cancer, as an indicator of prostate cancer.

Where the body-fluid sample is seminal fluid, the assayed level of GPC3 indicative or prostate cancer is preferably in a range between 1 and 10 ng/ml. Where the body-fluid sample is blood or serum, the assayed level of GPC3 indicative or prostate cancer is preferably in a range between 1 and 10 ng/ml.

In one embodiment of the method, the assaying step may involve applying the body fluid to a solid-phase immunoassay device, the level of GPC3 in the sample may be indicated qualitatively by a colorimetric or fluorometric indicator, and the determining may include comparing the indicator with a known standard.

For use in staging the treatment of prostate cancer in a human, the level of assayed GPC3 is indicative of the stage of the cancer in the subject.

In a related aspect, the invention includes a diagnostic device for use in for screening for prostate cancer in a human subject, or staging treatment of prostate cancer in a subject. The device includes a (i) structure for receiving a body-fluid sample from the subject, (ii) an anti-GPC-3 binding antibody associated with the structure and capable of reacting with body-fluid received in the structure, to produce, in combination with other reagents associated with the structure, a detectable reaction indicative of the level of GPC3 in the sample, and (iii) a known-standard indicator against which the level of detectable reaction produced can be assessed as an elevated level associated with prostate cancer. For use in staging the treatment of prostate cancer in a human, the known-standard indicator includes two or more indicators that represent different levels of GPC3 associated with different stages of prostate cancer.

In one embodiment, the structure in the device includes a porous pad or strip having the anti-GPC3 binding protein embedded therein, for reaction with the fluid sample when the sample is applied to the pad, the detectable reaction is indicated by a colorimetric or fluorometric indicator, and the known standard indicator includes an indicia that represents a level of GPC3 corresponding to that associated with prostate cancer.

In another embodiment, the device includes an instrument for generating a signal related to the level of GPC3 produced, a microprocessor for comparing the signal with a know-standard signal value associated with prostate cancer, and a display for displaying an output of the microprocessor.

In still another aspect, the invention includes a histological method for examining human prostate tissue for the presence and extent of prostate cancer. The method includes staining the prostate tissue with an anti-GPC-3 binding protein labeled with a detectable marker, to attach the marker to the surface of tissue cells, and determining, based on an elevated distribution and extent of detectable marker with respect to the distribution and extent of marker in normal prostate cells, the presence and extent of prostate cancer in the tissue. The distribution and extent of detectable marker in the tissue may be used to determine the stage of cancer in the tissue, as a method of staging the patient for anti-cancer treatment.

Also disclosed is a method for identifying genetic mutations associated with an increased risk of prostate cancer. Here method is practiced by (a) extracting genomic DNA from human patients having prostate cancer, (b) for each extracted DNA, comparing the sequence of the DNA in a selected region 0-200 kbases upstream of the GPC3 gene on chromosome interval Xq26, with a homologous region of DNA from one or more wildtype individuals, and (c), by the comparing, identifying one or more mutations in the region associated with an increased risk prostate cancer.

For use in constructing a gene chip designed for genetic screening for risk of prostate cancer, this method further includes (d) for each mutation identified in step (c) producing a gene fragment capable binding selectively to genomic DNA fragments carrying that mutation, but not to corresponding wildtype DNA fragments, and (e) attaching the gene fragments constructed in step (d) at known positions on a chip-chip substrate.

In still another aspect, the invention includes a method of reducing tumor burden in a subject with prostate cancer, by exposing subject antigen-presenting cells to human GPC3 polypeptide or antigenic fragment(s) thereof, and by the exposing, stimulating and causing clonal expansion of memory CD4 helper cells, CD8 Tc cytotoxic lymphocytes and CD8 non-cytotoxic T-suppressor lymphocytes thereby causing expansion of GPC3 antigen-specific memory CD4 helper cells, GPC3 antigen-specific CD8 Tc cytotoxic lymphocytes and GPC3 antigen-specific CD8 non-cytotoxic T-suppressor lymphocytes in the subject.

The treatment method may be practiced by exposing the subject's antigen-presenting cells ex vivo to the human GPC3 polypeptide or antigenic fragment(s) thereof, under conditions effective to activate the cells, and injecting the activated cells into the subject. Alternatively, the method may be practiced by injecting the subject with the human GPC3 polypeptide or fragments thereof, carried in a suitable adjuvant.

In another immunotherapy treatment method, in accordance with the invention, a patient's body-fluid sample is assayed for the level of GPC3 protein in the sample, to determine from the assayed level, whether the subject has an elevated GPC3 level associated with prostate cancer. If the patient has such an elevated GPC3 level, the patient is treated by administering a therapeutically effective amount of a GPC3 binding agent effective, when bound to GPC3 on the surface of prostate cancer cells, to inhibit growth or viability of the cells. The GPC3 binding agent administered may be human or humanized anti-GPC3 antibody, effective, when bound to GPC3 on the surface of prostate cancer cells, to promote antibody-dependent cell cytotoxicity.

These and other aspects, objects, advantages, and features of the invention will become apparent to those persons skilled in the art upon reading the details of the invention as more fully described below.

DETAILED DESCRIPTION OF THE INVENTION

I. Definitions

The following terms have the definitions given below, unless otherwise indicated in the specification.

"Screening" for prostate cancer, in accordance with the present invention, means testing individuals for a level of GPC3 that is indicative of prostate cancer or an elevated risk of prostate cancer.

"Staging" treatment of prostate cancer, in accordance with the present invention, involves determining the stage of prostate cancer in an individual, based on the level of GPC3 detected, and tailoring the treatment to that stage. There are four recognized stages of prostate cancer, which are defined by the degree of localization of cancer cells. In addition, prostate cancer may be defined as early stage at which the cancer is responsive to a number of hormonal-based therapies, and a later, more serious androgen-independent stage.

II. Prostate Cancer and GPC3 Expression

A. Identification of GPC3 as an Oncogene in a Retroviral Mutagenesis Screen.

A number of cancer genes (oncogenes and tumor suppressor genes) associated with prostate cancer were identified in a high throughput manner using proviral tagging in mice. In proviral tagging, mice are infected with a retrovirus that does not contain an oncogene (e.g., murine leukemia virus, MLV or murine mammary tumor virus, MMTV)(20-24). Recently, the host range of this approach has been broadened by the use of a transposon (25, 26).

During retroviral infection, the virus integrates into the cellular genome and inserts its DNA near or within genes, which leads to various outcomes: (i) The insertion site is too far away from a protooncogene and thus does not activate it. In this case, there will be no selection for that cell. (ii) The provirus inserts within 200 kb of a protooncogene, but not within the gene (type 1). Here, either the viral promoter or the viral enhancer increases the expression level of the protooncogene. (iii) The provirus inserts within a gene, destroying or altering its function (type 2). There will be no selection for a cell that contains either type 1 and type 2 insertion events in a gene that is not a protooncogene or tumor suppressor gene. If integration results in the formation of a tumor, genes adjacent to the integration site can be identified, and classified as either protooncogenes or tumor suppressor genes (20). A tumor suppressor may be scored if a retrovirus lands within a gene and truncates or destroys it. In these cases, the suppressor may be haplo-insufficient, or alternatively, the mutation on the other allele is provided spontaneously by the mouse. The integration event may also lead to more complex consequences, such as a dominant negative effect of the truncated gene product or the transcription of anti-sense or microRNA.

Figure 1:
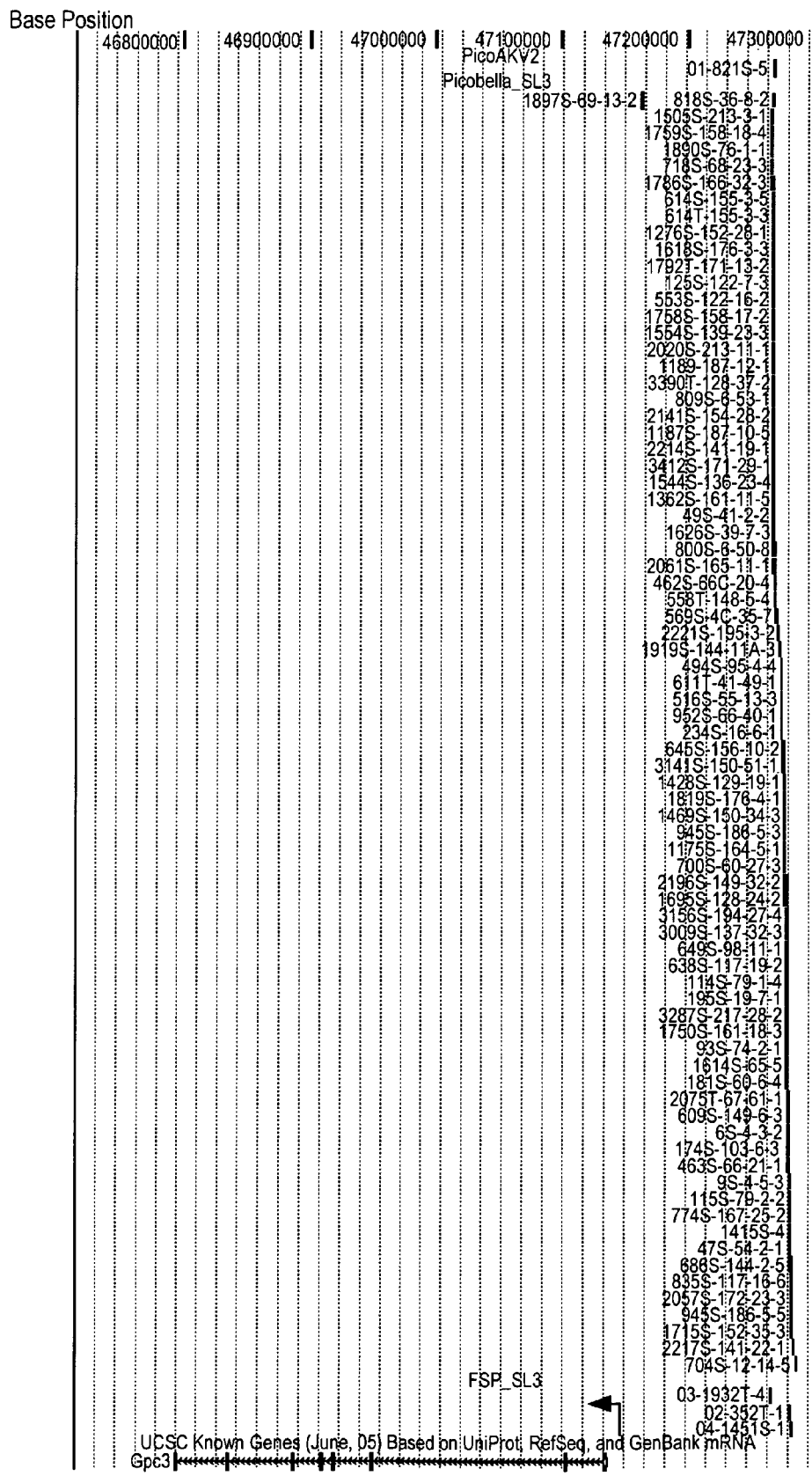
FIG. 1 shows the genomic organization of the mouse Gpc3 locus, as view by a customized screen print of the UCSC genome web site browser (March 2005 version of the mm6 gene assembly). Top, base position on chromosome X. Vertical handle bars in red, green and blue represent the retroviral insertions into the locus in 82 independent tumors.

In a screen with T lymphotropic virus SL3-3, 81 independent tumors were recovered that contained proviral integrations distributed over a range from 25 to 152 kb from the 5' end of the Gpc3 gene (FIG. 1, "Picobella_SL3" and "FSP_SL3"; green and blue bars). Similarly, in a screen with B lymphotropic virus Akv1-99, one tumor was recovered that contained a proviral integration within the same region (FIG. 1, "PicoAKV2"; red bar). These integrations cause the overexpression of the Gpc3 gene. These studies demonstrate that prostate cancer is associated with GPC3 overexpression, indicating that the gene functions as an oncogene in prostate cancer.

B. Expression of GPC3 in Human Prostate Tumors and Normal Tissue

Figure 2A:
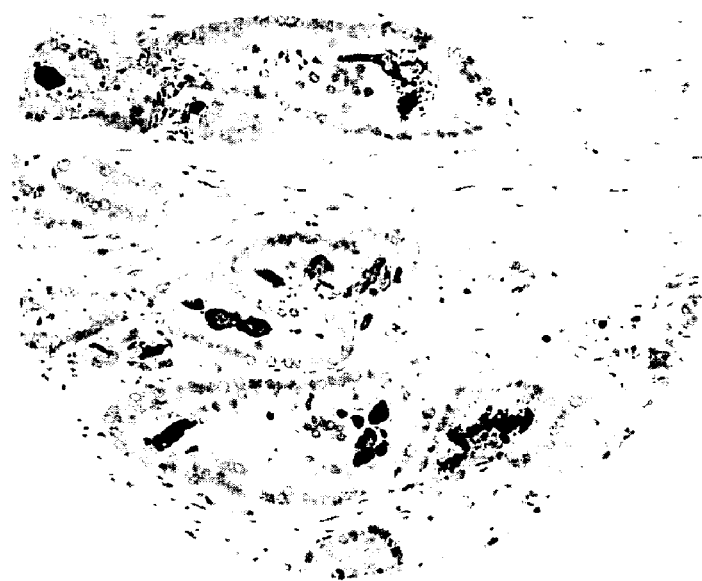
FIGS. 2A and 2B shows immunohistochemical stains of human prostate tumor (2A) and matched normal tissue from the same patient (2B). The polyclonal rabbit antibody serum used reacts with 2 peptide epitopes: DLFIDKKVLKVAH-VEHEET (amino acid residues 365 to 383, encoded by exon 4, and defined herein as SEQ ID NO:1) and LAYDLDVD-DAPGNSQQ (amino acid residues 526 to 541, encoded by exon 8, and defined herein as SEQ ID NO: 2)
Figure 2B:
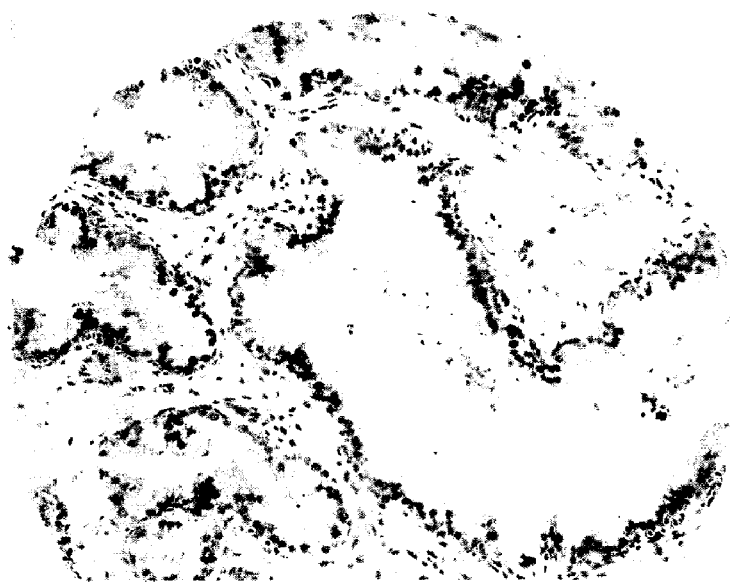

The mutations that were identified as causal in mouse tumor formation increased the steady-state level of protein expression. To confirm that overexpression of the GPC3 gene product is characteristic of prostate cancer, GPC3 protein was assayed in situ using an anti-GPC3 antibody, prepared as described above. Briefly, tissue samples from the ductile epithelium in normal and cancerous human tissue were exposed to unlabeled rabbit anti-GPC3 antibody under standard in situ labeling conditions. After washing the cells to remove unbound antibody, the tissue was stained with a horseradish peroxidase polymer-conjugated anti-rabbit secondary antibody (Zymed Laboratories), and viewed by photomicroscopy, with the results shown in FIGS. 2A (cancerous tissue) and 2B (normal tissue). As seen, GPC3 overexpression in prostate cancer leads to a higher concentration of GPC3 in the lumen of the ducts (FIG. 2A). More generally, the invention provides a histological method for examining human prostate tissue for the presence and extent of prostate cancer. In the method, prostate tissue is stained with a labeled anti-GPC-3 binding protein, e.g., fluorescence-labeled anti-GPC3 antibody (see Section II below), to attach the marker to the surface of tissue cells. The presence and extent of prostate cancer in the tissue is then determined based on an elevated distribution and extent of detectable marker with respect to the distribution and extent of marker in normal prostate cells.

As will be seen in Section IV below, elevated levels of GPC3 antigen, as an indicator of prostate cancer, increased risk of prostate cancer, or the stage of prostate cancer, can be assayed directly from a body-fluid sample, e.g., seminal fluid or a blood sample.

III. Preparation of Anti-GPC3 Antibody

This section describes production of anti-GPC3 antibodies useful for diagnostic and therapeutic purposes, as described further in the sections below. The anti-GPC3 antibody used in the present invention can be obtained by any a variety of conventional methods as a monoclonal, polyclonal, or recombinant antibody. One preferred antibody, particularly for diagnostic use, is a mouse monoclonal antibody, prepared according to wellknown hybridoma methodology. Briefly, human GPC3 may be first obtained, for example, by expressing the GPC3 (MXR7) gene as disclosed by Lage, H. et al. (Gene 188 (1997), 151-156). The purified GPC3 protein is as an immunogen. Alternatively, a partial peptide of GPC3 can be used as a sensitization antigen. The partial peptide can be obtained by chemical synthesis from the amino acid sequence of human GPC3. Two GPC3 sequences that may be employed are: DLFIDKKVLKVAHVEHEET (SEQ ID NO: 1; amino acid residues 365 to 383, encoded by exon 4) and LAYDLDVDDAPGNSQQ (SEQ ID NO: 2; amino acid residues 526 to 541, encoded by exon 8).

Anti-GPC3 antibodies useful in diagnostic applications may be labeled with a variety of detectable labels, including detectable reporters, such as enzymes for enzyme-linked immunosorbent assays (ELISA), detectable particles, such as gold particles and reporter-carrying liposomes, colorimetric or fluorescent reporters, radiolabels, and labels such as a biotin label by which secondary detectable labels, such as a reporter-labeled streptavidin label can be attached. In some assay formats, an unlabeled anti-GPC3 antibody, for example, a mouse IgG antibody, is detected by reaction with a labeled antibody, e.g., a labeled anti-mouse IgG antibody.

For therapeutic uses, human monoclonal antibodies having binding activity to glypican 3, (see Japanese Patent Publication (Kokoku) No. 1-59878 B (1989)) can be produced by sensitizing in vitro human lymphocytes with GPC3, and causing the sensitized lymphocytes to fuse with the human-derived myeloma cells having a permanent division potential. Alternatively, GPC3 as an antigen can be administered to a transgenic animal having all the repertories of a human antibody gene to obtain anti-glypican 3 antibody-producing cells, and then human antibodies for GPC3 may be obtained from the immortalized anti-GPC3 antibody-producing cells (see International Patent Publication Nos. WO 94/25585, WO 93/12227, WO 92/03918 and WO 94/02602).

In still other methods, human or humanized antibodies specific against GPC3 antigen can be prepared by recombinant technique, such as have been reported (see, for example, U.S. Pat. Nos. 6,090,382 and 6,258,562).

IV. Diagnostic Methods and Reagents

In one aspect, the invention includes a method of screening for prostate cancer in a human subject, or staging treatment of prostate cancer in a subject, by assaying a body-fluid sample from the subject for the level of GPC3 protein in the sample, and determining from the assayed level, whether the subject has an elevated GPC3 level associated with prostate cancer, as an indicator of prostate cancer.

Preferred body-fluid samples are (a) seminal fluid and (b) blood. Where seminal fluid is assayed, the assayed level of GPC3 indicative or prostate cancer is in a range between 1 and 10 ng/ml. Where blood is assayed, the assayed level of GPC3 indicative or prostate cancer is in a range between 1 and 10 ng/ml.

The assay may be carried out by any of a variety of assay methods used for detecting body-fluid antigens, including ELISA techniques, homogeneous assays, for example, involving fluorescence quenching, and a variety of solid-phase sandwich assays in which the GPC3 antigen is captured on by an anti-GPC3 antibody carried on a solid support, and the immobilized antigen-antibody complex is labeled with a second anti-GPC3 antibody, e.g., a second antibody carrying a colorimetric or gold-particle reporter.

Figure 3A:
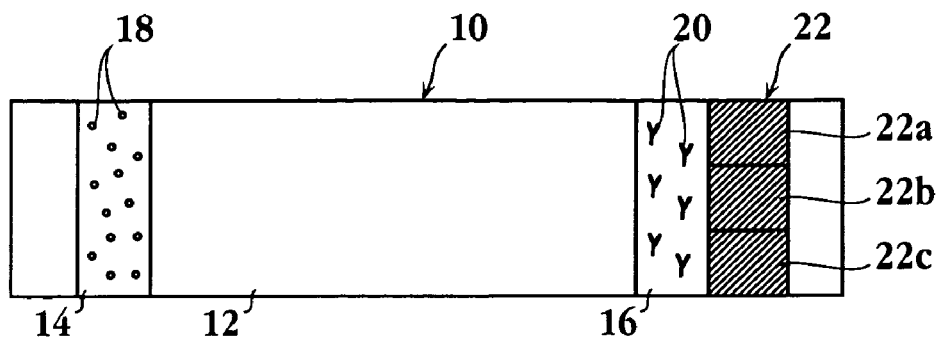
FIGS. 3A and 3B show a solid-phase diagnostic device for determining GPC3 levels in a human patient, at initial (3A) and final stages (3B) of the assay.
Figure 3B:
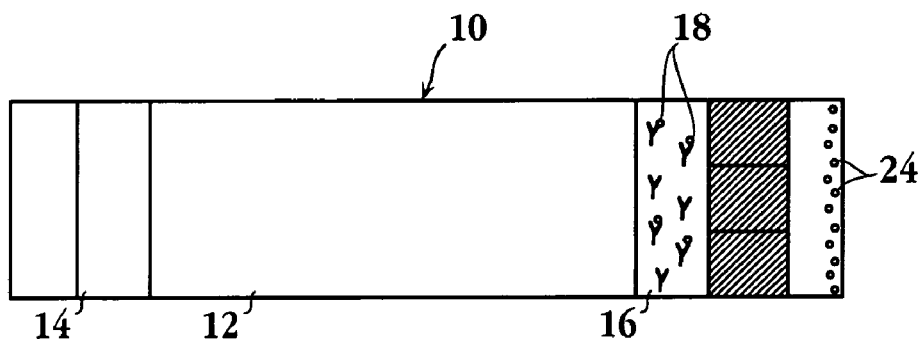

FIGS. 3A and 3B illustrate a solid-phase assay strip constructed in accordance with an embodiment of the invention, suitable for carrying out a sandwich immunoassay of the type just mentioned, and shown in initial and final assay states, respectively. The strip, indicated generally at 10, includes a porous support or pad 12 having a sample-application zone 14 in an upstream region of the support and a sample-detection zone 16 in a downstream region. The sample-application zone includes a detectable anti-GPC3 antibody reagent, e.g., anti-GPC3 antibodies labeled with gold particles, and carried in the zone in an unbound, i.e., non-immobilized form. This reagent is indicated by solid circles, such as at 18. Anti-GPC3 antibodies, which may be the same or different from those in the labeled antibody reagent, are immobilized to the solid support within the detection zone, and are indicated by the "Y" shapes, such as at 20.

Also shown is a reference zone 22 which is located adjacent the detection zone and has one or more colored or shaded regions corresponding to different assay levels of GPC3 in a body-fluid sample. In the embodiment shown, zone 22 includes three regions 22a, 22b, and 22c, corresponding to an assayed level of GPC3 (a) below that associated with prostate cancer, (b) corresponding to a lower threshold level associated with prostate cancer, and (c) a level that is substantially higher, e.g., 2-3 times, higher than the threshold layer in region 22b, respectively. These three regions provide a known standard indicator against which the level of detectable reaction produced can be assessed as a level associated with prostate cancer. Together, the assay strip and reference zone constitute an assay device for use in screening for prostate cancer in a human subject, or for staging treatment of prostate in a human subject.

In operation, a known volume of a body-fluid sample to be tested is added to the sample-application zone of the strip, where it diffuses into the zone, allowing the antibody reagent to react with GPC3 antigen in the sample to form an antigen-antibody complex. This complex and unbound antibody reagent then migrate downstream by capillarity toward the detection zone, where the antigen-antibody complex is captured by the immobilize antibody and the unbound reagent is carried to the end of the support, as indicated at 24. As can be appreciated, the higher the concentration of antigen in the body fluid, the higher the density of captured reagent in the detection zone and the greater the color or intensity in this zone. This color or intensity produced in the detection zone is compared with the standards in the reference zone to determine a qualitative level of GPC3 associated with the presence or absence of prostate cancer. If a sub-threshold level of GPC3 is observed in the assay, the subject can be classified in a low-probability category for the presence of cancer. If a threshold or higher level of antigen is observed, the subject may be recommended for additional testing and/or more frequent testing.

In another embodiment, the assay device includes an assay strip like that described above, but where the known-reference indicator is provided by a strip-reader instrument reader having (i) a reader slot for receiving the assay strip, (ii) a light source and an optical detection, e.g., a spectrophotometric detector, for detecting an assay-related optical condition at the detection zone of the assay strip, (iii) an electronics or processor unit which records and processes a signal from the optical detector, and converts the signal to an assayed level of GPC3, and (iv) a user display screen or window. The instrument may report the actual GPC3 body-fluid sample detected, allowing the operator to compare the displayed value with known standard indicator levels provided with the assay strip or instrument, to assess whether the subject has an elevated GPC3 level associated with prostate cancer, or to assess the possible stage of the cancer, for purposes of treatment design. Alternatively, the instrument itself may contain stored known-standard indicator levels which can be compared internally with an assayed level to generate an output that indicates whether an elevated GPC3 level associated with prostate cancer has been detected, or to indicate the stage of the cancer.

V. Identifying Genetic Mutation Associated with Prostate Cancer

In another aspect, the invention provides a method for identifying mutations associated with increased risk of prostate cancer in a human subject. The method is based on the finding discussed in Section IIA above that many virally induced mutations introduced into the region 0-200 kbases upstream of the GPC3 gene of chromosomal interval region Xq26 were associated with prostate cancer.

In practicing the method, genomic DNA is extracted from human patients having prostate cancer, preferably including patients from men representing different racial and age groups, and in particular, patients that are known to have a family history of the disease, e.g., fathers or other close male relatives with prostate cancer. The Xq26 from the long arm of the X chromosome is isolated according to known methods, and these fragments are sequenced by standard sequencing techniques that may involve, in one known methods (i) cutting the fragments with selected endonucleases, (ii) cloning the cut fragments in a suitable cloning vector, e.g., single-stranded sequencing vector, and sequencing the resulting clones.

Mutations are one or more sites along the region are identified by comparing each of the 200 kbase upstream sequences with sequences from the same region derived from normal (wildtype) males with no known family predisposition to prostate cancer. Preferably sequences from a number of wildtype men are determined to ensure a true wildtype sequence. For each extracted DNA, the patient and wildtype sequences are compared to identify mutations in the patient sequences, and thus mutations that are likely associated with increased risk of prostate cancer.

Figure 4:
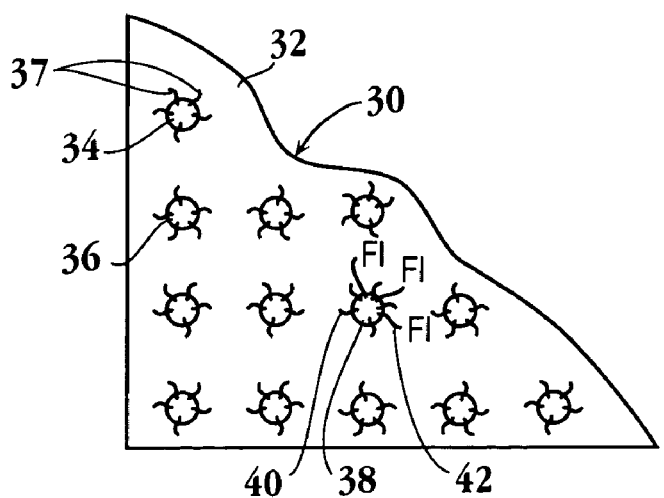
FIG. 4 shows a portion of a gene chip useful for diagnosing genetic predisposition to prostate cancer, constructed in accordance with the present invention.

Once a large number of these mutations are identified, e.g., at least 50-200 or more, they may be used in constructing a genetic screening device, e.g., a gene chip, useful for screening individuals for genetic predisposition to prostate cancer. In one embodiment, the device includes a gene chip, such as shown at 30 in FIG. 4, having an array of regions, such as regions 34, 36, each containing bound known-sequence fragments, such as fragment 37 in region 34. The fragments or probes are preferably 25-70 bases in lengths, and each includes one of the above-identified mutations upstream of the GPC3 gene that is associated with prostate cancer. In particular, the array sequences are designed in length and sequence to bind to those Xq26 mutations identified above, but not to associated fragments. Gene-chip construction, and detection of mutant sequences with such chips, are well known.

In a typical genetic-screening procedure, patient cells are obtained, genomic DNA is extracted, and Xq26 sequence regions of interest are amplified by standard PCR, employing fluoresceinated probes. The amplified material is then reacted with the chip-array sequences, under suitable hybridization conditions, and the array surface is washed to remove unbound material, then scanned with a suitable chip reader to identify any mutated sequences associated with prostate cancer. The figure shows binding of a labeled genomic DNA fragment, indicated at 42, to an array region 38 having bound probe molecules 40. Detection of a fluorescent signal in this array region is diagnostic of a known genetic mutation in the critical upstream GPC3 region of Xq26 interval and may be diagnostic of a genetic predisposition to prostate cancer.

In an alternative embodiment, the mutated identified as above are used to construct a set of molecular inversion probes (MIPs) capable of identifying the presence of genomic mutations by the steps of: The construction and use of MIPs for identifying genetic mutations have been described (see, for example, Wang, et al., Nucleic acids research (England) 2005, Vol. 33, p. 21).

VI. Treatment Methods and Pharmaceutical Preparations

The invention also includes methods for treating, e.g., reducing the tumor burden in a human subject with prostate cancer. In one approach, a GPC3 antigen, e.g., full length GPC3 or an antigenic peptide, such as one of the GPC3 peptides disclosed above, is used to activate immune cells that participate in inducing cytotoxic T cells specific against prostate tumor cells. This may be done, in one embodiment, by exposing antigen-presenting cells obtained from the patient ex vivo with the GPC3 antigen, under conditions effective to activate the cells, e.g., in the presence of GM-CSF. Once activated ex vivo, the cells are reintroduced into the patient, where the activated cells are effective in stimulating clonal expansion of cytotoxic T cells against the tumor. This immunotherapy approach is described, for example, in U.S. Pat. No. 6,080,409 and pertinent references cited therein.

Alternatively, the GPC3 antigen may be administered to the patient as a vaccine, typically present in a suitable adjuvant, such as one containing GM-CSF. The peptide vaccine is effective to stimulate and causing clonal expansion of memory CD4 helper cells, CD8 Tc cytotoxic lymphocytes and CD8 non-cytotoxic T-suppressor lymphocytes, causing expansion of GPC3 antigen-specific memory CD4 helper cells, GPC3 antigen-specific CD8 Tc cytotoxic lymphocytes and GPC3 antigen-specific CD8 non-cytotoxic T-suppressor lymphocytes in the subject.

Preparation of antigen-containing compositions suitable for injection, and suitable antigen doses for immuno-stimulation of cytotoxic T cells have been described in a number of patents and literature publications on T-cell induction by immunotherapy. Those methods are applicable in the present method involving GPC3 antigen for the treatment of prostate cancer. Following treatment, the patient is monitored for change in status of the cancer, typically by a combination of a tumor-visualization procedure, such as MRI or CAT scan, and levels of prostate-related antigens, including GPC3 itself.

In a second general immunotherapy approach, a patient diagnosed with prostate cancer is first confirmed as having elevated levels of GPC3, according to assay methods described above. If the subject tests positive in this assay, he is treated by administration of anti-GPC3 antibody. Preferably the antibody is a human or humanized antibody, prepared as described above, and is administered by IV or subcutaneous injection in a suitable physiological carrier. The antibody dose is preferably 1 to 10 mg/injection, and the patient is treated at intervals of every 14 days or so. During treatment, the patient is monitored for change in status of the cancer, typically by a combination of a tumor-visualization procedure and levels of prostate-related antigens, as above. The treatment may be carried out in combination with other prostate-cancer treatments, including drug or radio-isotope therapy, and may be continued until a desired diminution in tumor size is observed.

While the invention has been described with respect to particular embodiments and applications, it will be appreciated that various changes and modification may be made without departing from the invention as claimed.

Sequences

SEQ ID NO:1: DLFIDKKVLKVAHVEHEET (amino acid residues 365 to 383 of human GPC3 antigen, encoded by exon 4 of the human GPC3 gene).

SEQ ID NO: 2: LAYDLDVDDAPGNSQQ (amino acid residues 526 to 541 of human GPC3 antigen, encoded by exon 8 of the human GPC3 gene).

It is claimed:

1. A method of screening human male subjects for prostate cancer, comprising the steps of:
(i) applying a body-fluid sample of blood, serum, seminal fluid, or prostate ductile fluid from a human male subject to a solid phase immunoassay device comprising an anti-GPC3 antibody;
(ii) quantifying the level of GPC3 protein in the sample;
(iii) identifying those male subjects in which the quantified level of GPC3 is in a range between 1 and 10 ng/ml; and
(iv) recommending those male subjects identified in step (iii) for additional or more frequent testing for prostate cancer.

2. The method of claim 1, wherein the body-fluid sample is seminal fluid.

3. The method of claim 1, wherein the body-fluid sample is blood or serum.

4. The method of claim 1, wherein in step (i) the level of GPC3 in the sample is indicated by a colorimetric or fluorometric indicator.

* * * * *